(12) United States Patent
Brahms et al.

(10) Patent No.: US 7,750,073 B2
(45) Date of Patent: Jul. 6, 2010

(54) USE OF THERMOPLASTIC ELASTOMERS IN A COMPOSITION AND COMPOSITIONS THEREOF

(75) Inventors: John C. Brahms, Morris Plains, NJ (US); Prithwiraj Maitra, Randolph, NJ (US); Tao Zheng, Nanuet, NY (US); David A. Binder, Saddle Brook, NJ (US)

(73) Assignee: Avon Products, Inc., New York, NY (US)

( * ) Notice: Subject to any disclaimer, the term of this patent is extended or adjusted under 35 U.S.C. 154(b) by 1231 days.

(21) Appl. No.: 11/314,634

(22) Filed: Dec. 21, 2005

(65) Prior Publication Data

US 2007/0142521 A1 Jun. 21, 2007

(51) Int. Cl.
*C08L 83/00* (2006.01)
*B05D 7/00* (2006.01)
*A61K 8/34* (2006.01)

(52) U.S. Cl. ............ 524/506; 524/499; 524/505; 523/111; 427/387; 424/61; 424/401

(58) Field of Classification Search ............ 523/111; 524/499, 505, 506; 424/61, 401; 427/387
See application file for complete search history.

(56) References Cited

U.S. PATENT DOCUMENTS

| | | | | |
|---|---|---|---|---|
| 3,787,531 A | * | 1/1974 | Dahlquist et al. | 525/92 K |
| 4,231,369 A | * | 11/1980 | Sorensen et al. | 604/336 |
| 5,214,093 A | | 5/1993 | Nell et al. | |
| 5,800,816 A | | 9/1998 | Brieva et al. | |
| 5,911,974 A | | 6/1999 | Brieva et al. | |
| 6,036,947 A | | 3/2000 | Barone et al. | |
| 6,071,503 A | | 6/2000 | Drechsler et al. | |
| 6,074,654 A | | 6/2000 | Drechsler et al. | |
| 6,139,823 A | | 10/2000 | Drechsler et al. | |
| 6,274,152 B1 | | 8/2001 | Brieva et al. | |
| 6,340,466 B1 | | 1/2002 | Drechsler et al. | |
| 2003/0147819 A1 | | 8/2003 | Watanabe | |
| 2004/0223933 A1 | | 11/2004 | Hiwatashi et al. | |
| 2007/0055014 A1 | * | 3/2007 | Lu et al. | 525/64 |

FOREIGN PATENT DOCUMENTS

| EP | 1329483 A2 | 7/2003 |
|---|---|---|
| EP | 1440680 A1 | 7/2004 |

OTHER PUBLICATIONS

ExxonMobil Product data sheet on PureSyn HIgh Viscosity PAO, May 2009.*
Fried, J.R., Polymer science and technology, Upper Saddle River, NJ:Printice-Hall PTR, 1995, ISBN 01368556-1-X. pp. 100, 136,314 and 321.
Sartomer Company, Technical Data Sheet: Wingtack? 95 Molten Aliphatic C-5 Petroleum Hydrocarbon Resin, Aug. 2005 [Downloaded from www.sartomer.com Aug. 31, 2007.].
Colas, A. Silicones in pharmaceutical applications. Dow Corning Corporation, Form No. 51-993A-01, Copyright 1997, 2001, [Downloaded from www.dowcornng.com Aug. 31, 2007.] p. 4.

* cited by examiner

*Primary Examiner*—Fred M Teskin
(74) *Attorney, Agent, or Firm*—Joan M. McGillycuddy; Charles J. Zeller; Anthony M. Santimi

(57) ABSTRACT

Compositions and methods for the formation of physically cross-linked thermoplastic elastomeric films are disclosed. The disclosed films are long-lasting, flexible, transfer resistant, and water-proof. The film-forming compositions comprise a thermoplastic elastomer, a tackifier resin, and a volatile solvent useful for formulating cosmetics, personal care products, and pharmaceutical compositions.

34 Claims, No Drawings

USE OF THERMOPLASTIC ELASTOMERS IN A COMPOSITION AND COMPOSITIONS THEREOF

FIELD OF THE INVENTION

The present invention relates generally to compositions which form films on a surface and uses thereof.

BACKGROUND OF THE INVENTION

Cosmetics, personal care products, and pharmaceutical compositions that contain film-forming polymers intended for use on biological surfaces for improving adhesion, long lasting effects, and protecting skin and nails and colorants on skin and nails are commercially available. Cosmetic formulations including polymers such as thermoplastic elastomers as film formers which are easily removed using soap and water are exemplified in U.S. Publication No. 2004/0223933A1 and EP 144068033A1. The specific examples given in this case contain polymers in which at least one block of the polymer is water soluble or hydrophilic and charged. Although the art discuss the use of thermoplastic elastomers in cosmetic formulas to impart desirable film forming properties, thermoplastic elastomer copolymers are usually insoluble or less soluble in aqueous or alcoholic solvents, and therefore, generally thought to be inappropriate for polymeric cosmetic compositions.

U.S. Publication No. U.S. 2003/147819A1 and EP1329483A2 discuss the use of cosmetic body pigments in cosmetic compositions and in resin compositions. Thermoplastic elastomer resins, among numerous other polymers, are cited in these applications strictly in the context of their use as solid resins into which the pigments can be dispersed.

Thermoplastic elastomers are generally employed in areas where the melt to solid transition property is less important, such as for example, footwear, wire insulation, adhesives, etc. More specifically, thermoplastic elastomers are typically employed in applications where the polymer is heated above the melting temperature of the polymer's high melting domain. This renders the polymer liquid. As the polymer cools, the high melting domains form cross-links resulting in a network structure of physical rather than chemical cross-links. Such network structures form a swellable elastomeric structure that can be broken and reformed upon a temperature change. Other elastomeric structures are generally formed by chemical cross-links through, for example, condensation or free-radical chain transfer mechanism. These structures with chemical cross-links are not reversibly formed. Since thermoplastic elastomers generally rely on the use of high heat, as the prior art suggests, their application to cosmetic and skin care products is not apparent and inappropriate.

U.S. Pat. Nos. 5,800,816; 5,911,974; 6,036,947; 6,274,152; 6,071,503; 6,139,823; and 6,340,466 describe the use of a silicone resin, an MQ resin, in combination with one or more of a non-volatile or volatile silicone, non-volatile oil, silicone oil, silicone fluid, silicone gum, silicone wax, wax, cyclomethicone, or guerbet ester.

For compositions to perform satisfactorily, they must exhibit a number of desirable performance properties. Compositions are known which provide films on biological substrates, and which have desirable performance properties. Desirable characteristics of film-forming compositions include: good application, the production of a uniform film of desired sheen or gloss, good adhesion, a certain amount of flexibility, and good film strength to avoid cracking and flaking of the film, preferably in the absence of irritation of the skin, hair, and/or nails upon which the film-forming composition is applied.

Despite advances in film forming methods and compositions, there remains a need in the art for film forming compositions which provide long-lasting, transfer resistant, comfortable, highly flexible, tack-free, and water-proof films.

There is therefore a need for a method and composition for providing a film on a biological substrate that is durable, flexible, water and oil resistant, abrasion resistant, and transfer resistant for delivering actives, colorants, and the like.

It is further an object of the invention to provide cosmetic, personal care, and pharmaceutical compositions comprising compositions which form a durable, flexible, water and oil resistant, abrasion resistant, and transfer resistant film and deliver actives, colorants, and the like.

SUMMARY OF THE INVENTION

In accordance with the foregoing objectives and others detailed herein, the invention overcomes deficiencies associated with the prior art by providing in one embodiment of the invention, compositions comprising at least a thermoplastic elastomer, a tackifier resin, and a volatile solvent which form physical cross-linked films on biological surfaces.

In one embodiment, the composition of the invention, comprising a charge-neutral hydrophobic thermoplastic elastomer, a tackifier resin or mixture thereof, and a volatile solvent or mixture thereof, when applied to a biological surface, such as keratinous tissue, forms physically cross-linked films upon dissipation of solvents, and is water insoluble. The biological surface may be any surface to which cosmetics, personal care products, and pharmaceutical compositions are typically applied, including but not limited to skin, lips, hair, nails, and the like. The composition that is applied to keratinous surfaces invokes the formation of physical cross-links upon the evaporation or dissipation of the volatile solvent or mixture thereof. The resultant film is durable, flexible, water and oil resistant, abrasion resistant, transfer resistant, and long-lasting.

One embodiment of the invention provides a method of conveying flexibility, water resistance, oil resistance, abrasion resistance, and transfer resistance to keratinous tissue, by applying the composition of the invention to keratinous tissue; activating the composition by means known to one skilled in the art, such as but not limited to, heat, physically rubbing, and by altering pH levels; dissipating the volatile solvent or mixture thereof; forming a physically cross-linked film on keratinous tissue. The composition that is topically applied to keratinous tissue forms a durable, flexible, water resistant, oil resistant, abrasion resistant, and transfer resistant film when applied to keratinous tissue.

Another embodiment provides a method for forming a film on a keratinous surface by contacting the surface with the composition of the invention. The composition comprises a charge-neutral hydrophobic thermoplastic elastomer, a tackifier resin or mixture thereof, and a volatile solvent or mixture thereof, where the thermoplastic elastomer film former comprises a hard domain and an elastomer domain. Once the composition is applied to the keratinous surface, the composition is activated by heat, physically rubbing, or by changing the pH level, which thereby dissipates the volatile solvent or mixture thereof, and the resulting film has physical cross-links and is durable, flexible, water resistant, oil resistant, abrasion resistant, and transfer resistant.

These and other aspects of the present invention will become apparent to those skilled in the art after a reading of the following detailed description of the invention, including the illustrative embodiments and examples.

DETAILED DESCRIPTION OF THE INVENTION

The invention relates to a composition which comprises a thermoplastic elastomeric film former, tackifier resin or mixture thereof, and volatile solvent or mixture thereof, for delivering active ingredients, colorants, and the like by topically applying the composition to a biological substrate or surface. The composition may be a single phase organic composition, water in oil emulsion, or oil in water emulsion which ranges in viscosity from free flowing to semi-solid, and preferably water insoluble. The composition may be topically applied to keratinous tissue, including but not limited to hair, skin and nails, to form a durable or long-lasting, flexible, water resistant, oil resistant, abrasion resistant, and generally transfer resistant film on the keratinous tissue. Non-limiting examples of the topical compositions include cosmetics, hair products, medicinal preparations, insect repellents, and sun products.

Desirable characteristics of the resulting film formed by the compositions include: good application, the production of a uniform film of desired sheen or gloss, rapid drying time, good adhesion, a certain amount of flexibility, and good film strength to avoid cracking and flaking of the film, preferably in the absence of irritation of the skin, hair, and/or nails or other keratinous surfaces upon which the film-forming composition is applied.

One embodiment of the invention encompasses a composition which comprises a thermoplastic elastomer that is particularly useful as a film former, in combination with a tackifier resin or mixture thereof and volatile solvent or mixture thereof. The thermoplastic elastomer in the composition of the instant invention is charge-neutral and hydrophobic. While natural and synthetic polymers and mixtures thereof have been useful as film formers in cosmetic compositions, charge-neutral hydrophobic thermoplastic elastomers are particularly beneficial in forming a flexible, water and oil resistant, abrasion and transfer resistant, non-shrinking, non-tacky, and comfortable film. The thermoplastic elastomer film former may be present in the composition at about 0.1 weight % to about 90 weight %, preferably 0.5 weight % to about 70 weight %, and more preferably at about 0.7 weight % to 30 weight % based on the total weight of the composition. The thermoplastic elastomers of the inventive composition may complex with organic molecules such as dyes, ultraviolet absorbers, and drugs or actives, for delivery to the keratinous surface to which the composition is applied, thereby forming a coherent continuous film.

Generally, thermoplastic elastomers are multiphase compositions where at least one phase has a material that is hard at room temperature, but becomes fluid or less hard upon heating, i.e., the hard phase or domain. Another phase of the thermoplastic elastomer has a material that is softer, more like rubber at room temperature, i.e., the elastomer phase or domain. Thermoplastic elastomers may be block copolymers. The block polymer of the invention may have any form of diblock, triblock, and multi-block copolymer. The topical composition preferably has a thermoplastic elastomer of an A-B-A tri-block copolymer. For example, the block copolymer having a hard domain or block A (high $T_g$ block) and a soft, elastomer domain or block B (low $T_g$ block) in the form of an A-B diblock copolymer, an A-B-A tri-block copolymer, such as poly(styrene-b-elastomer-b-styrene), styrene-isobutylene-styrene (SIBS), styrene-silicone-styrene, and a multi-block copolymer structure (A-B)n, as well as branched block copolymers having a structure of $(A-B)_{nx}$ (where x represents an n functional joint). Thermoplastic elastomers are preferably A-B diblock copolymers, A-B-A triblock copolymers, $(A-B)_n$ multi-block copolymers, and mixtures thereof. More specifically, non-limiting thermoplastic elastomers include polyurethane/elastomer block copolymers, polyester/elastomer block copolymers, polyamide/elastomer block copolymers, polyethrimide/polysiloxane block copolymers, styrene copolymers, and any combinations thereof.

In a preferred embodiment, the thermoplastic elastomer is a linear A-B-A triblock type, such as but not limited to, styrene-butadiene-styrene, styrene-isoprene-styrene, or styrene-ethylenebutylene-styrene. More preferably, the thermoplastic elastomer used as a film former in the composition of the invention is styrene isobutylene styrene (SIBS).

The film-forming thermoplastic elastomers used according to the invention have a glass transition temperature ($T_g$) in a range which causes a soft and elastic film to be produced. Glass transition temperatures are the point at which the polymer or fragment thereof moves from a solid brittle state into a rubbery liquid state. As will be understood by one skilled in the art, the $T_g$ of various polymers may be determined through testing and by referring to the glass transition points which are described in commonly known and used references (see, Polymer Handbook, Eds. J. Brandrup, et al., 2 Volumes Set, Fourth Edition, John Wiley and Sons, Inc., June 2003; Introduction to Polymer Science and Technology, Eds. H. S. Kaufmnan and J. J. Falcetta, John Wiley and Sons, Inc., 1977) in order to understand this concept and to identify particular combinations of polymers or hard and elastomer phases, which would be useful in the invention.

In a further embodiment, any charge-neutral, non-polar, hydrophobic thermoplastic elastomer may be used as a film former in a composition, where one phase, preferably the hard phase, has a glass transition temperature ($T_g$) of about 40° C. or greater, preferably about 50° C. or greater, and still more preferably about 60° C. and the other phase, preferably the elastomer phase, has a $T_g$ less than about 25° C., preferably about 10° C. or lower, and more preferably about 0° C. or lower. Yet a further embodiment encompasses a thermoplastic elastomer where the two phases differ in $T_g$ by about 15° C., preferably by about 30° C., and more preferably by about 50° C. These characteristics enable the composition to be resistant to water and oil, and serve as a means for delivering active ingredients, such as but not limited to, colorants, UV absorbers, insecticides, and drugs in the form of a non-tacky, flexible, comfortable film.

In addition to glass transition temperatures, solubility parameters provide a numerical method of predicting the interaction between materials, such as liquids and polymers. They are useful in determining the suitability of polymers for particular applications and in formulating mixtures of solvents for specific purposes. A further embodiment of the invention relates to solubility parameters between the two phases or domains of the thermoplastic elastomer and/or between each of the phases and the volatile solvent or mixtures thereof. As will be understood by those of skill in the art, the solubility parameters for the thermoplastic elastomer phases and solvents or mixtures thereof may be determined, by referring to commonly known and used references, in order to form compositions of the invention. (see, for example, Allan F. M. Barton, Handbook of Solubility Parameters and Other Cohesion Parameters, Second Edition, CRC Press, Boca Ratan, Fla., 1991; Hansen, Charles M., "The Three Dimensional Solubility Parameter—Key to Paint Component Affinities: I. Solvents Plasticizers, Polymers, and Resins," Journal of Paint Technology, Vol. 39, No. 505, 1967; Hansen, Charles M., "The Three Dimensional Solubility Parameter—Key to Paint Component Affinities: II. Dyes, Emulsifiers, Mutual Solubility and Compatibility, and Pigments," Journal of Paint Technology, Vol. 39, No. 511, 1967; Hansen, Charles M., "The Three Dimensional Solubility Parameter—Key to Paint Component Affinities: III. Independent Calculations of the Parameter Components," Journal of Paint Technology, Vol. 39, No. 511, 1967).

In a further embodiment which is particularly suitable for achieving particularly good properties of a composition, the thermoplastic elastomers have a difference in solubility parameter between the hard phase and the elastomer phase of at least 0.5 $(cal/cc)^{1/2}$. The composition of another embodiment has a solubility parameter of at least one volatile solvent within about 0.2 $(cal/cc)^{1/2}$ of the thermoplastic elastomer, preferably the hard phase of the thermoplastic elastomer. In yet a further composition, at least one of the volatile solvents has a solubility parameter within about 0.2 $(cal/cc)^{1/2}$ of the thermoplastic elastomer, preferably the elastomer phase.

Similar to increasing the temperature of thermoplastic elastomers, dissolving the thermoplastic elastomers in a volatile solvent or mixture thereof, results in a loss of strength or the breaking of physical cross link. Although not to be bound by theory, it is believed that when a solvent in the composition evaporates, the composition essentially "dries" and regains its original integrity by forming physical cross-links. The thermoplastic elastomer of the invention generally forms a network structure through physical cross-links that can be broken and reformed; whereas chemical cross-links which are formed by other non-thermoplastic elastomeric polymers, cannot be reversibly formed.

More specifically, one way to apply a thermoplastic elastomer as a film former in compositions is to take advantage of the difference in solvation free energy density between the high $T_g$ and low $T_g$ melting domains. Another advantage of the inventive composition is that a separate structuring agent is not required. In particular, a solvent system that is compatible with the solvation energy of a mid-block copolymer (e.g., elastomer domain) and incompatible with that of an end-block copolymer (e.g., hard domain) provides for a primary film former as well as a structuring agent. Thus, the addition of a structuring agent is not necessary. By exposing the thermoplastic elastomer polymer to a solvent, preferably a volatile solvent or mixture thereof, that selectively solvates the high $T_g$ melting domains, the cross-linked gel structure can be temporarily disrupted. This state can be maintained in the product formulation during storage wherein the thermoplastic elastomer film former composition is a low viscosity, free flowing material. Upon application to, for example, skin, the volatile solvent that disrupts the physical cross-links evaporates resulting in the reformation of the physical cross-links and desired film structure. Since the melting temperature of high $T_g$ melting domains is significantly above body temperature, the only mechanism by which the film can be disrupted is by selective solvation. The most likely chemical insults a product film on skin will be exposed to are either highly hydrophobic (i.e., vegetable oil) or hydrophilic (i.e., water). These films may be resistant to insult by amphiphilic materials such as fatty acids and surfactants since they rely on surface energy reduction and consist of molecules with combined high and low hydrophilic components.

Volatile solvents produce a film exhibiting superior water-resistance, oil-resistance, and abrasion-resistance, and may be applied to, for example, nails, such as a nail enamel. The volatile non-polar solvent may be linear, cyclic, or branched having a boiling point below about 250° C., preferably having a boiling point less than about 200° C., more preferably less than about 175° C. at normal atmospheric pressure. The composition may be a single phase organic composition, water in oil emulsion or oil in water emulsion which ranges in viscosity from a free flowing solution to a semi-solid gel-like form. A preferred composition is water insoluble. The volatile non-polar solvent included in the composition of this invention may be, for example, a hydrocarbon, ester, silicone, or amide based organic solvent. The solvent or combinations thereof are preferably those that promote the temporary disruption of the physical cross-links in the composition. Although not wishing to be bound by any theory, it is believed that as the volatile solvent or mixture thereof, evaporates or dissipates, the physical cross-links of the thermoplastic elastomer which were temporarily broken, are then reformed, forming a film, upon contact with keratinous tissue. It is this film, itself and in combination with other components of the composition, that provide the unique characteristics of the compositions of the invention.

The preferred solvents depend on the particular thermoplastic elastomer used in the invention. The solvent may be used in conjunction with one or more additional solvents conventionally used compositions as are well known in the art. The particular solvents may be selected and considered to be compatible with the film forming thermoplastic elastomers present in the composition in amounts which facilitate the temporary breaking of the thermoplastic elastomer physical cross-links and once the volatile solvent or mixture thereof evaporates, allow the physical cross-links to reform. Typically, the topical composition of the invention comprises an acceptable volatile solvent or a mixture of volatile solvents in addition to the thermoplastic elastomer film former and tackifier resin, enabling the composition to retain its gel, liquid, or semi-solid form.

In one embodiment with respect to the solvent portion in a thermoplastic elastomer composition, at low concentrations of thermoplastic elastomers, such as less than or equal to about 5 weight % in a composition, the composition must have a volatile solvent or mixture thereof that is compatible with the elastomer domain. This composition may optionally also have a combination of one or more non-volatile solvents. Furthermore, the composition may optionally also have a solvent or mixture thereof, that is compatible with the hard domain.

Whereas, at high concentrations of thermoplastic elastomers, such as more than or equal to about 5 weight % in a composition, the composition must have a volatile solvent or mixture thereof that is compatible with the hard domain. This composition may optionally have a volatile or non-volatile solvent, or combinations thereof, that are compatible with the soft domain.

The amount of solvent, including solvent mixtures as set forth above, necessary to ensure an acceptable product viscosity (i.e., ease of applying without running) depends on the nature of the solvent and the nature and amounts of the other ingredients, such as, in particular thermoplastic elastomers and other film forming ingredients, plasticizers, thickeners, solids, etc. The amount of volatile solvent may be readily determined by routine experimentation. In general, however, amounts of solvent(s) suitable for the purpose of this invention fall in the range of from about 1% to about 90% by weight of the composition, preferably about 5% to about 80% by weight of the composition, more preferably about 10% to about 70% by weight of the composition.

Non-limiting examples of volatile solvents useful in the compositions described herein include aliphatic, olefinic and aromatic hydrocarbons, chlorinated hydrocarbons, ketones, acetates, ether, chloroform, alcohol, esters, silicones and combinations thereof. These solvents are volatile in that they evaporate quickly upon application of the composition to keratinous tissue, such as but not limited to, skin, lips, hair, and nails.

As will be understood by those of skill in the art, the solvent and solubility conditions may be altered in order to prepare a composition which has the desired properties. As will be further appreciated by the skilled practitioner, the solubility parameters and glass transition temperatures, $T_g$, can be approximated by the formulas as known in the art, depending on a number of parameters, such as the thermoplastic elastomer, solvent, and other ingredients and conditions.

One of ordinary skill in the art may be able to determine the solubility parameters and choose a solvent based on the block copolymer chosen for the envisaged application. More information regarding solubility parameters and solvents useful in the processing of specific block copolymers is available from the various manufacturers of block copolymers. Additional discussions of polymer solubility parameter concepts are presented in: Encyclopedia of Polymer Science and Technology, Vol. 3, Interscience, New York (1965) and Encyclopedia of Chemical Technology, Supp. Vol., Interscience, New York (1971), the disclosures of which are hereby incorporated by reference.

In yet another embodiment, tackifier resins may be used to modify the viscosity and elastic properties of a composition which affect the performance of the composition by obtaining optimal tack/adhesion and cohesive force which are key for long lasting wear properties. Residual tackiness of the thermoplastic elastomer composition may be advantageously provided by the selection of the tackifying resin. The inventive compositions described herein typically include resins or blends of tackifying resins.

A further embodiment of the invention encompasses a composition having a thermoplastic elastomer, a solvent or mixture thereof, and a tackifier resin or mixture thereof, where the tackifier resin is a silicone resin. For example, the composition may include a tackifier resin that is a silicone resin or a non-silicone resin, or a mixture of tackifier resins comprised of silicone resins, or a mixture of silicone resins and non-silicone resins. In yet another embodiment, the composition may have a silicone-based thermoplastic elastomer, a solvent or mixture thereof, and a tackifier resin or mixture thereof, where the tackifier resin is a silicone resin or non-silicone resin.

Silicone resins in thermoplastic elastomer film-forming compositions provide additional transfer resistance without compromising the comfort of the inventive composition that is durable, flexible, water and oil resistant, abrasion resistant, and transfer resistant for delivering actives, colorants, and the like. More specifically, use of a triblock copolymer, silicone resin, and volatile solvent in a composition, such as a cosmetic compound, provides properties including long-lasting durability and transfer resistance, while maintaining a comfortable flexible consistency. For example, a composition having an SIBS thermoplastic elastomer, a silicone resin, and volatile solvent results in a composition that is specifically increased in water and oil transfer resistance without loss of comfort especially on the skin and lips. Non-limiting examples of silicone resins include MQ, MT, T, and combinations thereof. MQ resins have the general formula, $M_xQ_y$, where M is $R_1R_2R_3SiO_{1/2}$; Q is $SiO_{4/2}$; $R_1$, $R_2$ and $R_3$ are each independently, or in combinations thereof, $C_{1-30}$ straight or branched chain alkyls or phenyls or alkylfluoros or aminos, or combinations thereof. The ratio of M to Q (x to y) can range from about 0.7 to about 2. MT resins have the general formula, $M_xT_y$, where M is $R_1R_2R_3SiO_{1/2}$; and T is $RSiO_{3/2}$, where R, $R_1$, $R_2$ and $R_3$ are, but not limited to, alkyl, phenyl, alkylphenyl, alkylfluoro, amino, and combinations thereof.

The ratio of M to T (x to y) can range from about 0.7 to about 3, preferably the M to T ratio is about 0.7 to about 3. Another silicone resin is a T resin having a general formula of $RSiO_{3/2}$ where R is alkyl, phenyl, alkenyl, alkyl phenyl, amino, alkylfluoro, or alkyl phosphates.

Without being bound by theory, a silicone resin forms a three-dimensional (3-D) cage or ladder-like structure, which depending on its specific functional groups, may either migrate towards and self assemble at the elastomer domain or at the hard domain in an A-B-A triblock copolymer composition. For example, in a composition having an SIBS thermoplastic elastomer and a silicone tackifier resin of either a MQ or T resin where its functional group is a phenyl group, self assembly of the 3-D structure along the hard domains may be observed. In another example, functional groups that are alkyl or branched alkyl result in resin migration towards the elastomer mid-block domain. In yet another example, fluoro or alkyl perfluoro are selected as a functional group of silicone resins, which results in the formation of phase-separated microdomains providing additional oil and/or water resistance. Additionally, other desired properties include a high level of gloss which is provided by alkyl-, phenyl-, or amino-modified MQ or T resins. Without being bound by theory, alteration of the $T_g$ of the silicone resins may be accomplished by using a combination of these resins in order to further modify the film morphology in order to produce a composition that is comfortable, long-lasting, transfer resistant, highly flexible, tack-free, and water-proof.

A further embodiment of the invention relates to compositions comprising a tackifier resin, selected as described below, wherein the tackifier resin is present in an amount of about 0.1% to about 50%, preferably from about 3% to about 40%, and more preferably from about 5 to 30% by weight of the total composition, or blend of tackifier resins in a ratio of 1:10 and preferably a ratio of 1:5.

As would be understood by one skilled in the art, residual tackiness of a composition at room temperature and at normal atmospheric pressure may be adjusted by selecting a suitable tackifier resin or mixture thereof. The $T_g$ and the compatibility of the resin are the major factors controlling the adhesive properties of a polymer/resin combination. $T_g$ has a relationship with softening point and it is more useful for formulators to be aware of the $T_g$ value than the softening point value of a tackifier resin for formulation purposes. As an example, use of the correct $T_g$ tackifier resin and the right resin concentration in a polymer provide the desired properties. Preferred tackifier resins, or mixtures thereof, have a softening point between about 5° C. and about 250° C., more preferably between about 30° C. and about 200° C. Whereas, preferred tackifier resins have a $T_g$ between about −60° C. and about 200° C., preferably between about −40° C. and about 170° C., and most preferably between about −30° C. and about 150° C.

In one embodiment, at least one of the tackifier resins has a solubility parameter within about 1 $(cal/cc)^{1/2}$, preferably within about 0.5 $(cal/cc)^{1/2}$, and more preferably within about 0.2 $(cal/cc)^{1/2}$ of each of the elastomer phases of the thermoplastic elastomer in a composition. In another embodiment, at least one of the tackifier resins has a solubility parameter within about 1 $(cal/cc)^{1/2}$, preferably within about 0.5 $(cal/cc)^{1/2}$, and more preferably within about 0.2 $(cal/cc)^{1/2}$ of each of the hard phases of the thermoplastic elastomer in a composition.

Increased transfer resistance and long-lasting effects may be achieved by the addition of a second tackifier resin, such as a silicone resin. The $T_g$ of the second resin preferably ranges from about −60° C. to about 250° C., and more preferably from about −40° C. to about 200° C. However, these parameters apply preferably when the second tackifier resin is a silicone resin. In addition to the $T_g$ of the second tackifier resin, its solubility parameter is important in the inventive composition. Preferably, the difference in solubility parameters between the thermoplastic elastomer and the second tackifier resin should be at least about 1 $(cal/cc)^{1/2}$ or greater, and more preferably at least about 1.5 $(cal/cc)^{1/2}$ or greater.

Non-limiting examples of suitable tackifier resins may include any one or mixtures thereof of natural or modified rosins such as, for example, gum rosin, wood rosin, tall-oil rosin, distilled rosin, hydrogenated rosin, dimerized rosin, and polymerized rosin; glycerol and pentaerythritol esters of natural or modified rosins such as, for example, the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; copolymers and terpolymers of natural terpenes, for example, styrene/terpene and alpha methyl styrene/terpene; polyterpene resins, or those resulting from terpene hydrocarbons, such as the bicyclic monoterpene known as pinene, hydrogenated polyterpene resins; phenolic modified terpene resins and hydrogenated derivatives thereof, for example, bicyclic terpenes; aliphatic petroleum hydrocarbon; hydrogenated aliphatic petroleum hydrocarbon resins; alicyclic petroleum hydrocarbon resins and the hydrogenated derivatives thereof; and aliphatic/ aromatic or cycloaliphaticlaromatic copolymers and their hydrogenated derivatives.

Additional non-limiting examples of preferred tackifier resins include, rosin esters, rosinate esters, hydrocarbon resins obtained by oligomerization of the C5 and C9 fractions of petroleum, such as Wingtack® 10 and Wingtack® 85 (Sartomer Comp. Inc.; Exton, Pa.), aliphatic resins, terpene resins, terpene-phenolic resins, polyterpenes (e.g., Sylvagum® TR 90; Arizona Chemical; Jacksonville, Fla.), aromatic resins, synthetic C5 resins, mixtures of synthetic C5-C9 resins, coumarone-indene resins, copolymers of alpha-methyl styrene and vinyl toluene, and silicone resins, such as but not limited to, MQ resin (e.g., SR1000 from GE® Silicones; Waterford, N.Y.), MT resin, and T resin (Dow Corning® 2-2078 Fluid from Dow Corning Corp.; Midland, Mich.), and mixtures thereof.

In a preferred embodiment of the invention, the composition of the instant invention relates to a composition comprising a charge-neutral hydrophobic thermoplastic elastomer film former, a tackifier resin or a mixture thereof, and a volatile solvent or a mixture thereof, which can overcome these disadvantages and produce a film having properties such as good adhesion, stability, flexibility, wearability, non tackiness, good retention, transfer resistance, abrasion resistance, and low migration overtime. The inventive composition provides a physically cross-linked film on a keratinous surface when the volatile solvent or mixture thereof evaporates at a rate that preferably allows the formation of a continuous film free from imperfections having the desired performance properties as described above.

The inventive composition may be used in a variety of cosmetic, personal care products, and pharmaceutical formulations comprising an effective amount of a thermoplastic elastomer, a tackifier resin or mixture thereof, and volatile solvent or mixture thereof, necessary to obtain the desired properties. The skilled artisan will be able to determine the effective amount and type of thermoplastic elastomer film former, tackifier resin or mixture thereof, and volatile solvent or mixture thereof desired depending on the application and degree of durability, flexibility, applicability, wearability, uniformity, sheen or gloss, adhesion, water and oil resistance, transfer resistance, and abrasion resistance, preferably in the absence of irritation. One skilled in the art will also be able to determine the amount and type of thermoplastic film former, tackifier resin or mixture thereof, and volatile solvent or mixture thereof, and additional ingredients needed to obtain a stable cosmetic or pharmaceutical product, depending on the application. A stable cosmetic or pharmaceutical product is one of sufficient stability to enable effective commercialization of the cosmetic or pharmaceutical product.

In another embodiment, the compositions of the invention may be used to hold or bind onto the surface, topical coatings, actives and functional ingredients. The active or functional ingredients may include colorants, pigments, ultraviolet filters, moisturizing agents, fragrance, insecticides, pharmaceutical agents and other active or functional ingredients known in the cosmetic or pharmaceutical arts.

A further embodiment of the invention relates to a composition, preferably a topical liquid, gel, foam, cream, lotion, or, semi-solid, that is a cosmetic, a personal care product, a pharmaceutical or medicinal formulation, an insect repellent, or a sun product, where the composition comprises at least a thermoplastic elastomer film former, a tackifier resin or mixture thereof, and a volatile solvent or mixture thereof. The composition is water resistant, oil resistant, abrasion or rub resistant, and transfer resistant, flexible, non-tacky, glossy, durable, adhesive, provides a moisture barrier, and capable of binding and/or delivering one or more active components, such as but not limited to, a colorant, a dye, a ultraviolet absorber, a moisturizer, a biologically active agent, a insecticide/pesticide, and an organic or inorganic active agent. For example, the composition of the present invention is sweat- and water-resistant, including treated swimming pool water, fresh water, and ocean water. The composition is also smudge resistant and does not flake. The composition may be used in products, such as but not limited to, sun care, skin care, color cosmetics, mascaras, hair products (shampoos, conditioners, hairspray, mousses and dyes/colorants), a mascara, a nail enamel, a lip coloring product, a lip gloss, a foundation, eye make-up, a skin care product, a personal hygiene product, and a topical drug or active delivery.

The present invention relates to a composition, in particular a cosmetic composition, with transfer resistance, long wearing, and waterproof properties. The composition comprises a thermoplastic elastomer, in particular, di-block, tri-block, or multi-block copolymers, a tackifier resin or mixture thereof, and a volatile solvent or mixture thereof, and also relates to cosmetic and pharmaceutical products containing this composition.

Many cosmetic compositions including pigmented cosmetics such as foundations, concealers, mascaras, lipsticks, and other cosmetic, insect repellents, and sunscreen lotions leave soft oily films that can rub off or transfer quite easily. Compositions are therefore capable of becoming deposited, at least in part, by contact onto certain items, such as, for example, a glass, a cup, an item of clothing or the skin. Upon deposition, compositions leave a mark on the item. The result is less than optimal and requires application of the composition to be repeated regularly.

Although there are several transfer resistant cosmetic compositions that are known in the art, the majority of these compositions still need to be improved. These make-up compositions known in the art which have high transfer resistance generally comprise fatty substances, volatile oils, in particular volatile silicone oils and/or volatile hydrocarbon oils. Additionally, the majority of these transfer-free compositions is tacky; thus, the application and spreadability of the compositions are not ideal for cosmetics.

Besides transfer resistance, compositions must maintain stability. Often times film formers used in the art are mixed with a solvent to function as a thickener. However, the formulations which result can present a problem if the solvent in these thickeners migrate out of the gel matrix causing an instability of the formulation. Therefore, there remains a need for a transfer resistant stable composition, which also possesses desirable properties, such as but not limited to, ease of application, comfort, flexibility, durability, non tackiness during and after application, abrasion resistance, oil resistance, and water resistance.

The compositions of the invention provide excellent transfer resistance, durability, long wearing and waterproof properties in a broad range of applications. These applications include, but are not limited to, pigmented cosmetics, including foundations, concealers, mascaras, eye liners, eyeshadows, lipsticks, lip glosses, blushes; nail varnishes; hair sprays, gels and mousses, sunscreen lotions, moisturizing lotions, lotions with active ingredients, and fragrance. The products of the present invention is particularly useful in any cosmetic, personal care, or pharmaceutical application which relates to formation of a flexible film that adheres strongly to keratinous surfaces.

In a preferred embodiment, the thermoplastic elastomer film former of the invention are water insoluble, can be processed at room temperature, provide good adhesion to the skin, and are tack free. It is also preferred that the thermoplastic elastomer film former be compatible with the other ingredients in the composition.

The compositions of the invention are also effective in providing water resistance. The compositions may thereby minimize washing off of the active or functional ingredients, which is particularly useful in sun products and mascaras. The compositions may also retard dehydration of the skin by forming an occlusive film and reducing transepidermal water loss especially in moisturizers.

In a one embodiment, the compositions may provide a film barrier between the skin and the environment, where the film contains the active and/or functional ingredients. The film formed by the composition may increase the activity of the functional ingredients such as the SPF and UV light protection and/or block the effect of the humidity and the environment.

In yet another embodiment, the composition of the invention may additionally include any additive usually employed in the field envisaged such as antioxidants, perfumes, essential oils, stabilizers, cosmetic active substances, moisturizers, vitamins, essential fatty acids, lipophilic sunscreens, liposoluble polymers, and especially hydrocarbon polymers such as polyalkylenes and polyacrylates for improving smoothness or spreadability, water and oil resistance, transfer resistance, or other cosmetic or pharmaceutical properties desired by one of skill in the art. Non-limiting examples of optionally added ingredients include: emollients, thickening agents, for example, clays, or organoclays, silicas, cellulose derivatives, plasticizers, gels, oils, waxes, preservatives, solvents, surfactants; hectorites; synthetic polymers such as an acrylic polymer or an associative polymer of the polyurethane type; gums and in particular xanthan gum; spreading agents; dispersants; preservatives, in particular water-soluble preservatives; anti-foaming agents; wetting agents; ultraviolet-screening agents; perfumes; fillers; cosmetic or pharmaceutical active agents; moisturizers; vitamins and derivatives thereof; and biological materials and derivatives thereof. If the softness and elasticity of the composition are to be increased still further, it is also possible to add a plasticizer which is commonly added for cosmetic materials. Suitable materials may include both low-molecular weight and also high-molecular weight plasticizers which are optionally used, solubilized, or dissolved in a co-solvent.

Suspending and thickening agents typically include waxes, silica gels, gums, clays, fumed silica, fatty acid soaps, and various hydrocarbon gels, and other ingredients that when incorporated into the formulation remain on the surface of keratinous tissues. Non-limiting examples of ingredients, such as emollients, that may preferably be used in the compositions of the invention include glycerine, propylene glycol, cyclomethicone, dimethicone, and emollients and other similar ingredients disclosed in the International Cosmetic Dictionary and Handbook Vols. 1 and 2. Eds. Wenninger, J. A. and G. N. McEwen, Cosmetic, Toiletry, and Fragrance Association, Washington DC, 2000, which is hereby incorporated by reference.

For colored or pigmented products, the ratio of thermoplastic film former, tackifier resins, volatile solvents, and additional ingredients may be adjusted for maximizing adherence to and water, oil, and transfer resistance of the keratinous substrate or surface. An important consideration is the ratio of pigments to the amount of film former. A pigment should be understood to mean inorganic or organic, white or colored particles. Coloring agents that may be used in the practice of the invention may include pigments, lakes, and dyes which are well known in the art and are disclosed in the Cosmetic Ingredient Handbook, First Edition, J. M. Nikitakis, et al., Cosmetic, Toiletry, and Fragrance Association, Washington DC, 1988, the contents or which are hereby incorporated by reference.

Non-limiting examples of organic pigments include, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-Fe2O3, y-Fe2O3, Fe3O4, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable coloring agents include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and any other pigment or treated pigment known in the cosmetic arts.

Fillers and mother-of-pearl may also be added to said formulations to modify the texture of the composition and the matte/gloss appearance. Fillers should be understood to mean lamellar or nonlamellar, inorganic or synthetic, colorless or white particles. Mother-of pearl should be understood to mean iridescent particles produced especially by certain mollusks in their shell or else synthesized. Pearling agents that may be used in the practice of the invention include mica, iron oxides, titanium dioxide and any other pearling agent known in the cosmetic arts.

Although some of these materials may include an oily feeling and increased spreadability, as observed with some esters and organic sunscreens, the overall composition of the invention maintains its desired properties of transfer resistance, abrasion resistance, water and oil resistance, durability, flexibility, applicability, wearability, uniformity, sheen or gloss, drying time, adhesion, preferably in the absence of irritation. The person skilled in the art will of course take care to choose the optional additional compounds and/or their quantities in such a way that the advantageous properties of the composition according to the invention are not, or are substantially not, impaired by the envisaged addition(s). In embodiments where these materials are added to the formulations of the invention to enhance the spreadability and the emollience of the product, however, it is preferred that the above materials be present in low enough concentrations for the formulation to retain its desired properties. These ingredients may be selected variously by the person skilled in the art in order to prepare a composition which has the desired properties, for example, consistency or texture. The choice of thermoplastic elastomer film former, additional ingredients, and their concentrations may also be adjusted to vary the desired properties.

This technology and the inventive compositions are applicable to a wide variety products, including but not limited to: lipstick, lipgloss, mascara, foundation, sunscreens insect repellants, nail enamel, as well as skin care products such as masks, sun screens and insect repellants. In particular, the composition of the invention may include a cosmetic formulation. One embodiment of the invention relates to cosmetic foundations, where the formulation of a cosmetic foundation may contain, in addition to the composition of the invention, additional thickening agents and emollients in an amount that provides coverage and achieves the other desired properties.

Another embodiment of the invention is mascara, which employs the composition of the invention and produces increased stability and adherence to keratin surfaces, such as eyelashes. Mascara using the composition of the invention may also provide greater wear resistance, improved water resistance, and improved cosmetic properties.

A further embodiment of the invention includes lotions such as suntan lotion or sunblock. Lotions employing the composition of the invention may provide increased transfer resistance and water resistance. Lotions using the composition may also provide greater wearability.

Yet another embodiment of the invention includes eyeliner products. Eyeliners employing the composition of the invention may provide increased stability and adherence to eyelid tissue. Eyeliners using the composition of the invention may also provide greater water resistance and improved cosmetic properties.

Another embodiment is a make-up composition for the lips employing the composition of the invention which provides a homogeneous film that has a light texture and remains comfortable to wear throughout the day. The preferred lip make-up is not tacky or sticky, nor does it transfer, migration, or stain, but is long-lasting, soft, supple, elastic, flexible, and comfortable on the skin.

The packaging and application device for any embodiment of the invention is chosen and manufactured by persons skilled in the art on the basis of their general knowledge, and adapted according to the nature of the composition to be packaged. Moreover, the type of device to be used may be in particular linked to the consistency of the composition, in particular to its viscosity; it may also depend on the nature of the constituents present in the composition, such as the presence of volatile compounds.

In yet a further embodiment, a method of conveying durability, flexibility, oil resistance, water resistance, abrasion resistance, and transfer resistance to keratinous tissue, comprising: applying the composition of the instant invention having at least a charge-neutral hydrophobic thermoplastic elastomer film former, tackifier resin or mixture thereof, and a volatile solvent or mixture thereof, to keratinous tissue such as but not limited to the skin, hair, and nails; activating the topical composition by, for example, heat, physically rubbing, or by pH; dissipating the volatile solvent; and forming physical cross-links, in an amount effective to convey durability, flexibility, oil resistance, water resistance, abrasion resistance, and transfer resistance by forming a film when the composition is applied to the keratinous tissue.

The contents of all patents, patent applications, published PCT applications and articles, books, references, reference manuals and abstracts cited herein are hereby incorporated by reference in their entirety to more fully describe the state of the art to which the invention pertains.

As various changes may be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

EXAMPLES

The following examples further describe and demonstrate embodiments within the scope of the present invention. The examples are given solely for the purpose of illustration and are not to be constructed as limitations of the present invention, as many variations thereof are possible without departing from the spirit and scope of the invention.

Example 1

Lip Composition Prototypes

Table 1 provides lip composition prototype formulas based on a thermoplastic elastomer composition. Briefly, the lip compositions were prepared by stirring and heating at 105° C. for 15 minutes until homogeneous, 7% of styrene-isobutylene-styrene (SIBS) in isododecane. The mixture was also stirred while slowly cooled to about 25° C. The resulting soft gel structure was then used for preparing prototypes by adding additional ingredients typically used in cosmetic formulations.

The preformed soft gel of SIBS was mixed with 7% by weight of isododecane and heated to about 60° C. followed by the addition of pigments and sylvagum until homogenous. The mixture was then slowly cooled down to room temperature under constant stirring.

TABLE 1

Prototype Formulas

| ADDITIONS | PROTOTYPE FORMULA NO. | | | | |
|---|---|---|---|---|---|
| | 8442-45-I | 8442-45-II | 8442-45-III | 8442-45-IV | 8442-45-V |
| Pigments | 8% | 10% | 10% | 10% | 10% |
| SIBS (7% in Isododecane) | 20% | 10% | 30% | 40% | 50% |
| Sylvagum TR 90 (50% in Isododecane) | 50% | 60% | 40% | 30% | 20% |
| Isododecane | 22% | 20% | 20% | 20% | 20% |
| Total | 100% | 100% | 100% | 100% | 100% |

Example 2

Transfer Resistance of Lip Compositions

The transfer resistance of the lip compositions described in Example 1 was examined in comparison to the commercial lip coloring products Lipfinity™ (Procter & Gamble; Cincinatti, Ohio) and Lip polish™ (Maybelline; New York, N.Y.) using a modification of the transfer resistance testing protocol of U.S. Pat. No. 6,074,654, the disclosure of which is hereby incorporated by reference. The testing protocol used herewith is described below.

Transfer Resistance Test Method

This method was used to determine the water and oil transfer resistance and adhesion properties of a cosmetic film. This test predicted the ability of a cosmetic film to resist color transfer to objects contacting the skin. Such objects include clothing, handkerchiefs or tissues, napkins and implements such as cups, glasses and table wear, and oily fingers or objects such as oily foods.

Films formed by cosmetic compositions exhibit a degree of transfer resistance directly proportional to the hardness and solvent-resistance of the film. The hardness and solvent-resistance can be expressed as a function of the blot and rub test as described below. Standard safety measure should be observed when performing this test.

Equipment:
(1) Glass plates;
(2) Collagen sausage casing such as Nippi Casing F Grade;
(3) Constant humidity chamber adjusted to 95% relative humidity;
(4) Utility Knife;
(5) Ruler;
(6) Single-sided adhesive tape;
(7) Double-sided adhesive tape;
(8) 25 micron thickness slot draw-down bar;
(9) White Styrofoam dinner plate such as Amoco Selectables™ Plastic DL® Tableware;
(10) 1.5 inch diameter circular metal punch;
(11) 1 kilogram weight;
(12) Vegetable oil;
(13) Brush-tip cosmetic applicator; and
(14) Lint-Free Wiper, such as Kimwipes® EX-L.

Procedure:

(1) Prepared a 3×4 inch sheet of collagen sausage casing by hydrating it in a 90% relative humidity chamber for at least 24 hours.

(2) Removed the collagen sheet to ambient conditions and immediately wrapped it tightly around the glass plate. Attached the collagen sheet to the glass using adhesive tape. The collagen surface should be flat and free of wrinkles.

(3) Allowed the collagen-wrapped slide to equilibrate at ambient conditions for 24 hours.

(4) Applied thin (1 mil), uniform films of cosmetic formulations on the collagen surface.

(5) Allowed the cosmetic samples on the collagen to sit at ambient conditions for 1 hour.

(6) Using a pipette, three drops of vegetable oil were placed onto the right side of the film. Using another pipette, three drops of water were placed onto the left side of the film.

(7) Separately for the oil and water sections, the oil and water were distributed evenly over the film surface with cosmetic brush applicators, brushing lightly.

(8) Allowed the oil and water to remain on the film undisturbed for 15 minutes.

(9) Using a lint-free wiper, excess oil and water were carefully blotted from the film surface, applying as little pressure as possible during this step.

(10) Two disks were cut from a clean, white Styrofoam dinner plate using a 1.5 inch diameter circular punch. The surface and edges of each disk should be smooth and even.

(11) The disks from step (10) were separately and firmly attached one at a time with double-sided adhesive tape to the bottom surface of the 1 kg weight.

(12) The weight was set on top of the cosmetic sample applied to the collagen surface from step (5) above so that disk #1 is in contact with the oil section of the film and disk #2 is in contact with the water section of the film. It is important to position the weight gently so that excess force beyond 1 kg is not applied.

(13) Grasping the top of the 1 kg weight, the disk was carefully rotated through 360 degrees while maintaining the 1 kg force on the film. Do not lift or press the weight into the film during the rotating motion to the weight. The entire 360 degree rotation was completed within a time interval between 3 and 5 seconds.

(14) The weight was lifted straight up off the film surface and the disk was carefully removed from the weight avoiding damage to the disk.

(15) Color transfer on individual disks was based on visual assessment of the disks compared to commercial products as positive and negative benchmarks. The positive control used was Lipfinity™ (base coat) while the negative control used was the Lip Polish™ product.

(16) The criteria used in the "Star Grading System" for measuring the degree of transfer is explained in Table 2.

TABLE 2

Criteria used as grading scale for transfer

| Criteria | Scale |
| --- | --- |
| Less than Negative Control | * |
| Equal to or slight better than Negative control | ** |
| Between Negative and Positive Control | *** |
| About equal to positive control | **** |
| Better than positive control | ***** |

The results of the water and oil transfer resistance tests described above indicate that the lip gloss formulations of Example 1 comprising a thermoplastic elastomer exhibited water resistance equal to or better than the positive (Lipfinity™ base coat) control. However, with respect to the oil transfer, the lip gloss formulations of Example 1 did less than, equal to, or slightly better than the negative (Lip Polish™) control. Noticeably less pigment had transferred to the Styrofoam disk for the formulations of Example 1 than for the control products in the water resistance tests. Some of the formulations provide oil transfer resistance over the negative control which is the minimum satisfactory benchmark for oil transfer resistance. The results are quantified on the basis of the Star Grading System as shown below in Table 3.

TABLE 3

In vitro evaluation of lipgloss prototypes

| Prototype Formula No. | Transfer Resistance (Oil) | Transfer Resistance (Water) |
| --- | --- | --- |
| 8442-45-I | * | ***** |
| 8442-45-II | * | ***** |

TABLE 3

In vitro evaluation of lipgloss prototypes

| Prototype Formula No. | Transfer Resistance (Oil) | Transfer Resistance (Water) |
| --- | --- | --- |
| 8442-45-III | * | **** |
| 8442-45-IV | ** | **** |
| 8442-45-V | ** | ***** |

Example 3

The flexibility of the lip gloss formulations of Example 1 were examined using a modification of the flexibility testing protocol described in U.S. Pat. No. 6,074,654, the contents of which are hereby incorporated by reference. The flexibility of a cosmetic film is important to both the durability (long-wear) and comfort properties of a cosmetic film.

Flexibility was measured by the latex stretch test. This test predicts the ability of the color film to resist flaking or peeling which are indicators of the types of failure after application by movement of the skin during normal activities. The flexibility latex stretch test is based on the weight-loss measurement before and after the latex stretch.

Equipment:
(1) Ansell Industrial technicians unlined gloves (12" length, 17 mil) USDA Accepted #390, Size 9;
(2) Slanted Eyeshadow Brushes from Avon Products, Inc.
(3) Analytical balance (4 decimal places); and
(4) Ruler.

Procedure:
(1) A 1 inch wide band was cut from the wrist area of the glove, avoiding the ribbing and thumb.
(2) A 1×1 inch block was marked off in the center of the smooth side of the band, avoiding the embossed number.
(3) The latex band was weighed and the weight was recorded; hereinafter referred to as A.
(4) The initial weight of the cosmetic to be applied to the band was determined in order to produce a dried film weighing 20 mg. This was determined by dividing 20 mg by the weight percent of non-volatile material present in the cosmetic. For example, 40 mg of a cosmetic with 50% non-volatile content must be applied to the band in order to yield a 20 mg dried film.
(5) A clean eyeshadow brush was used to evenly apply the amount of cosmetic determined in step (4) over the 1×1 inch area of the band as marked in step (2).
(6) The combined weight of the latex band and applied cosmetic was weigh and recorded. The weight of the wet film with the latex band was referred to as B.
(7) The sample on the latex band from step (6) sat at ambient room conditions for 24 hours. The optimum test conditions to reliably correlate this test to the physical characteristics of the composition required a dry film. By dry it is meant that at least 90% of the volatile carrier of the cosmetic composition evaporated.
(8) The combination of the latex band A and the applied cosmetic film was weighed and recorded; hereinafter referred to as C. Subtract A from C to determine the dried film weight D (D=C−A). This weight should be 20±2 mg.
(9) The latex band was gently stretched so that the marked film length changed from 1.00 inches to 1.75 inches.
(10) Upon observing loosened film pieces on the latex band, the film pieces were removed from the latex band by vigorously wiping a clean eyeshadow brush across the surface of the film: 10 times wiping in a vertical direction and 10 times wiping in a horizontal direction.
(11) The latex band was carefully allowed to return to its approximate original shape.
(12) The weight of the latex band (with the remaining cosmetic) was recorded; herein referred to as E.
(13) A "Star Grading System" was used based on percentage weight loss ("PWL") to grade the flexibility of the films in Table 4 as follows:

TABLE 4

Criteria used as grading scale for flexibility test

| Weight Loss | Scale |
| --- | --- |
| 100–50% | * |
| 30–50% | ** |
| 15–30% | *** |
| 5–15% | **** |
| 0–5% | ***** |

The percent weight loss of the cosmetic film was calculated using the following equation:

Percent Weight Loss $(PWL) = [1 - (E-A)/(C-A)] \times 100\%$

For some very flexible films, the percentage weight loss may be negligible. Therefore, in some cases, due to some dust transferred from the brush, the PWL value may become negative (weight gain).

Steps (1) through (12) were repeated three times for each cosmetic formulation tested. The average of the three PWL values was determined; herein referred to as Average Percent Weight Loss ("APWL"). Low APWL values (i.e., 0-5%) corresponded to flexible films having a desirable adhesive and cohesive balance of the film.

In order to test the statistical difference between samples, at least 20 repeated measurements were conducted for each sample. A student T-test was run to calculate if there was significant difference between samples. The flexibility test results for the lip gloss formulations of Example 1 were quantified on the Star Grading System as shown in Table 5.

The results of the flexibility tests described above indicate that the lip gloss formulations of Example 1 comprising a thermoplastic elastomer exhibited excellent flexibility.

TABLE 5

In vitro evaluation of lip gloss prototypes

| Prototype Formula No. | Flexibility |
|---|---|
| 8442-45-I | ***** |
| 8442-45-II | ***** |
| 8442-45-III | ***** |
| 8442-45-IV | ***** |
| 8442-45-V | **** |

Example 4

Thermoplastic Elastomer Compositions

Additional examples of thermoplastic elastomers which were gelled with a solvent (isododecane) that selectively solvates the low melting region of the polymer were prepared with other ingredients as shown in Tables 6 and 7. Generally the solvent that solvates the high melting domain should be within 1.0 $(cal/cc)^{1/2}$ of the high melting block. In this example, the high melting block is styrene with a solubility parameter of 8.9-9.0 $(cal/cc)^{1/2}$. (ref: *Cosmet. & Toiletries*, 103:47-69, 1988). Butyl Acetate has a solubility parameter of 8.93. The low melting region, poly-isobutene, has a solubility parameter of 7.9-8.0 (*Polymer handbook* 4$^{th}$ ed. J. Brandrup, E. H. Immergut, E. A. Grulke eds., J. Wiley and Sons Inc. NY, 1999, pp704).

TABLE 6

Thermoplastic elastomer composition

| Ingredients | A | B | C | D |
|---|---|---|---|---|
| TiO$_2$ | 3% | 3% | 3% | 3% |
| Red 7 Calcium lake | 0.2% | 0.2% | 0.2% | 0.2% |
| Talc-14 | 4.8% | 4.8% | 4.8% | 4.8% |
| Iron oxide Red 34-2045 | 1.5% | 1.5% | 1.5% | 1.5% |
| Cosmetic Red oxide | 1.5% | 1.5% | 1.5% | 1.5% |
| SIBS | 10% | 10% | 10% | 15% |
| WingTack-10 | 0% | 5% | 10% | 10% |
| WingTack-85 | 0% | 5% | 10% | 15% |
| Isododecane | 79% | 69% | 59% | 49% |
| Total | 100% | 100% | 100% | 100% |

TABLE 7

Thermoplastic elastomer compositions

| Ingredients | E | F | G | H |
|---|---|---|---|---|
| TiO$_2$ | 3% | 3% | 3% | 3% |
| Red 7 Calcium lake | 0.2% | 0.2% | 0.2% | 0.2% |
| Talc-14 | 4.8% | 4.8% | 4.8% | 4.8% |
| Iron oxide Red 34-2045 | 1.5% | 1.5% | 1.5% | 1.5% |
| Cosmetic Red oxide | 1.5% | 1.5% | 1.5% | 1.5% |
| SIBS | 10% | 10% | 10% | 10% |
| WingTack-10 | 0% | 5% | 10% | 10% |
| WingTack-85 | 0% | 5% | 10% | 15% |
| Butyl Acetate | 5% | 10% | 15% | 20% |
| Isododecane | 74% | 59% | 44% | 34% |
| Total | 100% | 100% | 100% | 100% |

Example 5

Thermoplastic Elastomer Compositions with Silicone Resins

Examples of compositions with a SIBS thermoplastic elastomer and a mixture of tackifier resins, including silicone resins, were prepared with other ingredients as shown in Tables 8 and 9. These formulations have SIBS as the thermoplastic elastomer, isododecane as the solvent, and a tackifier resin mixture of: non-silicone resins, Sylvagum® TR 90 and Koboguard™ 5400, and silicone resins, GE® SR1000 (MQ Resin) and Dow Corning® 2-2078 Fluid (T Resin).

TABLE 8

Thermoplastic elastomer compositions with silicone resins

| Ingredients | 8442-48-1 | 8442-48-2 | 8442-48-3 | 8442-48-4 | 8442-48-5 |
|---|---|---|---|---|---|
| Pigments | 8 | 8 | 8 | 8 | 8 |
| SIBS (7% in Isododecane) | 50 | 50 | 50 | 50 | 50 |
| Sylvagum TR 90 (50% in Isododecane)) | 20 | 10 | 20 | 0 | 10 |
| Koboguard ™ 5400 (70% in Isododecane) | 0 | 20 | 0 | 20 | 20 |
| GE ® SR-1000 (MQ Resin) | 4 | 4 | 4 | 0 | 0 |

TABLE 8-continued

Thermoplastic elastomer compositions with silicone resins

| Ingredients | 8442-48-1 | 8442-48-2 | 8442-48-3 | 8442-48-4 | 8442-48-5 |
|---|---|---|---|---|---|
| Dow Corning ® 2-2078 Fluid (T Resin) | 0 | 0 | 4 | 4 | 4 |
| Isododecane | 18 | 8 | 14 | 18 | 8 |
| Total | 100 | 100 | 100 | 100 | 100 |

TABLE 9

Thermoplastic elastomer compositions with silicone resins

| Ingredients | SIBS – MQ3 | SIBS – MQ6 | SIBS III + MQ | SIBS + MQ |
|---|---|---|---|---|
| Pigments | 8 | 8 | 8 | 8 |
| SIBS (7% in Isododecane) | 50 | 50 | 30 | 50 |
| Sylvagum ® TR 90 (50% in Isododecane)) | 20 | 20 | 40 | 20 |
| GE ® SR-1000 (MQ Resin) | 3 | 6 | 9 | 9 |
| Isododecane | 19 | 16 | 13 | 13 |
| Total | 100 | 100 | 100 | 100 |

Example 6

Transfer Resistance of Thermoplastic Elastomer Compositions with Silicone Resins The transfer resistance of the thermoplastic elastomer compositions with silicone resins described in Example 5 was examined and tested as described in Example 2. Results are based on the criteria shown in Table 2. The results of the water and oil transfer resistance tests are shown in Table 10 for thermoplastic elastomer compositions with silicone resins. Most of these formulations demonstrate water transfer resistance. Formulations having silicone resin as one of the tackifier resins may be added to improve oil transfer resistance.

TABLE 10

In vitro evaluation of thermoplastic elastomer compositions with silicone resin

| Prototype Formula No. | Transfer Resistance (Oil) | Transfer Resistance (Water) |
|---|---|---|
| SIBS – MQ3 | ** | **** |
| SIBS – MQ6 | ** | ***** |
| SIBS III + MQ | ** | *** |
| SIBS V + MQ | ***** | * |

The content of all patents, patent applications, published articles, abstracts, books, reference manuals and abstracts, as cited herein are hereby incorporated by reference in their entireties to more fully describe the state of the art to which the invention pertains.

It should be understood that the foregoing description is only illustrative of the present invention. Various alternatives and modifications can be devised by those skilled in the art without departing from the invention. Accordingly, the present invention is intended to embrace all such alternatives, modifications and variations that fall within the scope of the appended claims.

What is claimed is:

1. A composition, comprising: a charge-neutral hydrophobic thermoplastic elastomer film former, a silicone resin or mixture of a silicone resin and a tackifier resin, and a volatile solvent or mixture of thereof, wherein the thermoplastic elastomer film former comprises a hard domain and an elastomer domain, wherein the composition is water insoluble, and wherein upon dissipation of the volatile solvent or mixture thereof, the thermoplastic elastomer film former is physically cross-linked, and the silicone resin is an MQ resin, an MT resin, or a T resin.

2. The composition of claim 1, wherein the thermoplastic elastomer film former is a block copolymer.

3. The composition of claim 2, wherein the block copolymer has at least two blocks.

4. The composition of claim 2, wherein the block polymer has at least three blocks.

5. The composition of claim 1, wherein the thermoplastic elastomer film former is an A-B-A tri-block copolymer.

6. The composition of claim 5, wherein the A-B-A tri-block copolymer is styrene-isobutylene-styrene.

7. The composition of claim 1 wherein the hard domain has a $T_g$ greater than or equal to about 40° C. and the elastomer domain has a $T_g$ of less than about 25° C.

8. The composition of claim 1, wherein the hard domain has a $T_g$ greater than about 50° C. and the elastomer domain has a $T_g$ of less than about 10° C.

9. The composition of claim 1, wherein the hard domain has a $T_g$ greater than or equal to about 60° C. and the elastomer domain has a $T_g$ of less than about 0° C.

10. The composition of claim 1, wherein the $T_g$ of the hard domain and elastomer domain differ by about 50° C.

11. The composition of claim 1, wherein the hard domain and the elastomer domain have a difference in solubility parameter of at least about 0.5 $(cal/cc)^{1/2}$.

12. The composition of claim 1, wherein the charge-neutral hydrophobic thermoplastic elastomer film former is present at about 0.1 wt % to about 90 wt % based on the total weight of the composition.

13. The composition of claim 1, wherein the charge-neutral hydrophobic thermoplastic elastomer film former is a poly(styrene-b-elastomer-b-styrene) block copolymer, a styrene-silicone-styrene block copolymer, a polyurethane/elastomer block copolymer, a polyester/elastomer block copolymer, a polyamide/elastomer block copolymer, a polyetherimide polysiloxane block copolymer, a styrene copolymer, or any combinations thereof.

14. The composition of claim 1, wherein the silicone resin or tackifier resin has a softening point between about 5° C. and about 250° C.

15. The composition of claim 1, wherein the tackifier resin has a $T_g$ between about −60° C. and about 200° C.

16. The composition of claim 1, wherein at least one of the tackifier resins has a solubility parameter within about 0.2 $(cal/cc)^{1/2}$ of each of the elastomer domains.

17. The composition of claim 1, wherein at least one of the silicone resins or the tackifier resins has a solubility parameter within about 0.2 $(cal/cc)^{1/2}$ of each of the hard domains.

18. The composition of claim 1, wherein the tackifier resin is a rosin, a modified rosin, a terpene, a polyterpene, a hydrocarbon resin obtained by oligomerization of the C5 and C9 fractions of petroleum, a coumarone-indene resin, a copolymer of an alpha-methyl styrene and a vinyl toluene, or any combinations thereof.

19. The composition of claim 1, wherein the silicone resin has a $T_g$ of about −60° C. to about 250° C.

20. The composition of claim 1, wherein the silicone resin has a solubility parameter of about 1 $(cal/cc)^{1/2}$ or greater.

21. The composition of claim 1, wherein at least one of the volatile solvents has a boiling point of less than about 250° C. at atmospheric pressure.

22. The composition of claim 1, wherein the volatile solvent or mixture thereof, selectively solvates each of the hard and elastomer domains of the thermoplastic elastomer.

23. The composition of claim 1, wherein at least one of the volatile solvents has a solubility parameter within about 0.2 $(cal/cc)^{1/12}$ of each of the elastomer domains.

24. The composition of claim 1, wherein at least one of the volatile solvents has a solubility parameter within about 0.2 $(cal/cc)^{1/12}$ of each of the hard domains.

25. The composition of claim 1, wherein the charge-neutral hydrophobic thermoplastic elastomer film former is less than or equal to about 5 weight % of the total weight of the composition, and the volatile solvent or mixture thereof is compatible with the elastomer domain.

26. The composition of claim 1, wherein the charge-neutral hydrophobic thermoplastic elastomer film former is greater than or equal to about 5 weight % of the total weight of the composition, and the volatile solvent or mixture thereof is compatible with the hard domain.

27. The composition of claim 1, wherein the volatile solvent is an aliphatic hydrocarbon, an olefinic hydrocarbon, an aromatic hydrocarbon, a chlorinated hydrocarbon, a ketone, an acetate, an ether, chloroform, an alcohol, an ester, a silicone, or combinations thereof.

28. The composition of claim 1, wherein the composition is a cosmetic, a medicinal preparation, an insect repellent, or a sunscreen.

29. The composition of claim 28, wherein cosmetic is a mascara, a nail enamel, a lip coloring product, a lip gloss, a foundation, eye make-up, a skin care product, or a personal hygiene product.

30. The composition of claim 1, further comprising an ingredient, wherein the ingredient is a colorant, a sunscreen, a moisturizer, a biologically active agent, a pesticide, or an organic or inorganic active agent.

31. The composition of claim 1, wherein the composition is a liquid, a gel, a foam, a cream, a lotion, or semi-solid.

32. The composition of claim 1, wherein the composition is durable, flexible, water and oil resistant, abrasion resistant, and transfer resistant.

33. A method of conveying durability, comfort, flexibility, water resistance, oil resistance, abrasion resistance, and transfer resistance to keratinous tissue, comprising: a) applying the composition of claim 1 to keratinous tissue; b) dissipating the volatile solvent or mixture thereof, and c) forming a physically cross-linked film, thereby conveying flexibility, water resistance, oil resistance, abrasion resistance, and transfer resistance when the composition is applied to the keratinous tissue.

34. A method for forming a film on a keratinous surface comprising: a) contacting said surface with a composition comprising: (i) a charge-neutral hydrophobic thermoplastic elastomer film former; (ii) a silicone resin or mixture of a silicone resin and a tackifier resin; and (iii) a volatile solvent or mixture of thereof, wherein the thermoplastic elastomer film former comprises a hard domain and an elastomer domain, and the silicone resin is an MQ resin, an MT resin, or a T resin: b) dissipating the volatile solvent or mixture thereof from the composition; and c) forming physical cross-links in the thermoplastic elastomer film former; thereby forming a film on the keratinous surface, wherein the film is flexible, water resistant, oil resistant, abrasion resistant, and transfer resistant.

* * * * *